United States Patent [19]

Calenoff et al.

[11] Patent Number: 4,528,267
[45] Date of Patent: Jul. 9, 1985

[54] FLUOROMETIRC ENZYME INHIBITION IMMUNOASSAY FOR MEASURING POTENCY OF ALLERGEN EXTRACTS

[75] Inventors: Emanuel Calenoff, Burlingame; Yuh-Geng Tsay, San Jose; Ruth M. Jones, Los Altos; Scott, John R., Mountain View, all of Calif.

[73] Assignee: Axionics, Inc., Calif.

[21] Appl. No.: 476,440

[22] Filed: Mar. 17, 1983

Related U.S. Application Data

[63] Continuation-in-part of Ser. No. 444,622, Nov. 26, 1982, , and a continuation-in-part of Ser. No. 434,061, Oct. 13, 1982.

[51] Int. Cl.³ .............................................. G01N 33/54
[52] U.S. Cl. .......................................... 435/7; 435/21; 436/513; 436/531; 436/532; 436/809
[58] Field of Search ....................... 436/513; 435/7, 21

[56] References Cited

U.S. PATENT DOCUMENTS

| | | | |
|---|---|---|---|
| 3,720,760 | 3/1973 | Bennich | 436/513 |
| 3,941,876 | 3/1976 | Marinkovich | 436/513 X |
| 4,002,532 | 1/1977 | Weltman | 436/513 X |
| 4,211,762 | 7/1980 | Huggins | 436/513 X |
| 4,331,650 | 5/1982 | Brewer | 436/513 |
| 4,347,311 | 8/1982 | Schmitz | 436/513 X |

OTHER PUBLICATIONS

"Enzyme-Immunoassay", E. T. Maggio, ed., p. 174, CRC Press, Inc., Boca Raton, 1980.

Primary Examiner—Sidney Marantz
Attorney, Agent, or Firm—William B. Walker

[57] ABSTRACT

An inhibition assay for measuring the potency of allergen extracts by incubating a mixture of allergen extract and reference allergen specific IgE in a buffered solution with an insoluble support to which reference allergen is adhered. The conjugated IgE adhering to the insoluble support is reacted with an enzyme labeled anti-IgE antibody and the enzyme label is contacted with a solution of a substrate which will yield a fluorescent product in the presence of the enzyme. The level of fluoresence in the solution is measured. The percentage of inhibition of the allergen specific IgE is determined from fluorescence levels measured for various extract concentrations.

23 Claims, 1 Drawing Figure

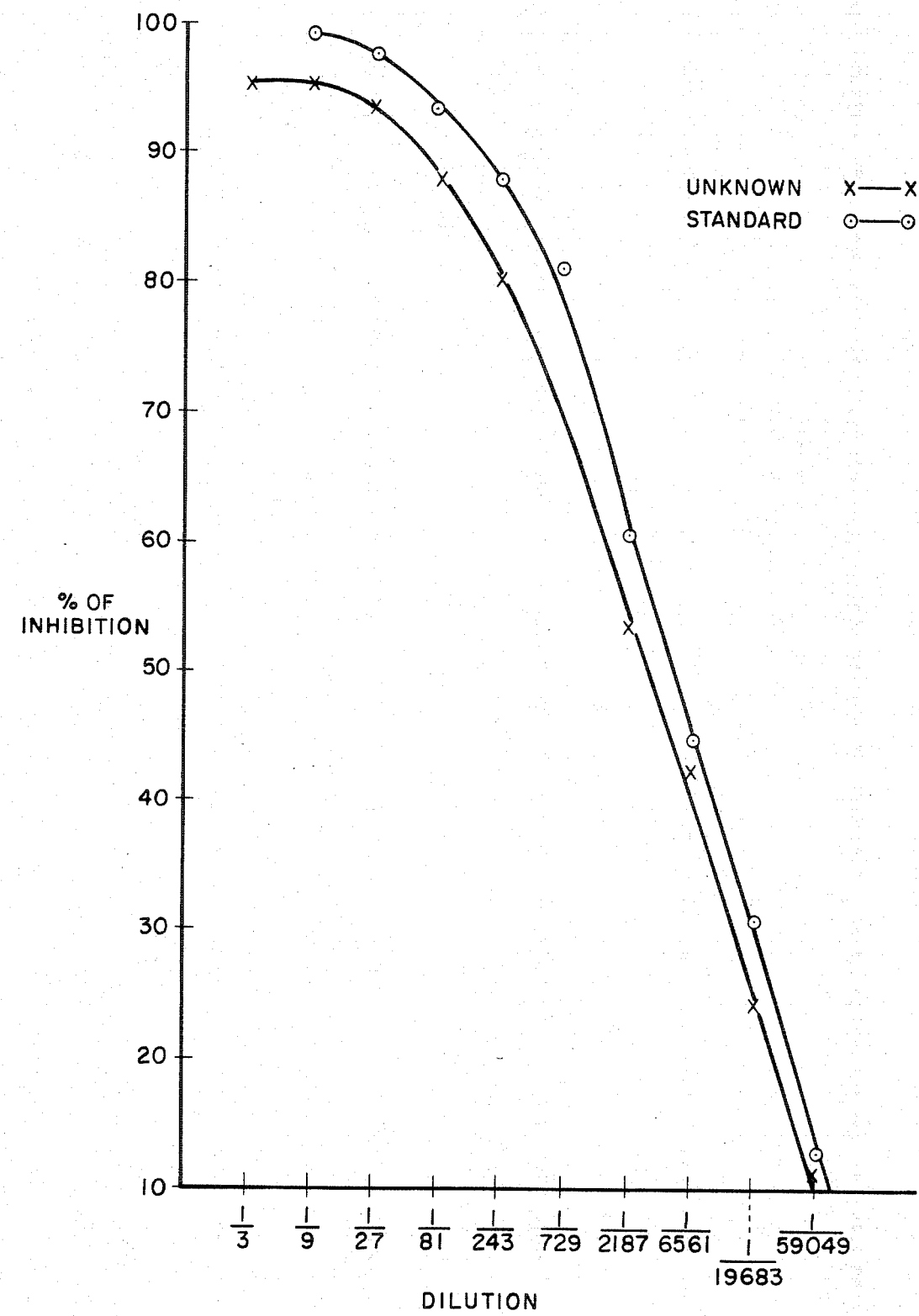

FLUOROMETIRC ENZYME INHIBITION IMMUNOASSAY FOR MEASURING POTENCY OF ALLERGEN EXTRACTS

RELATIONSHIP TO COPENDING APPLICATIONS

This application is a Continuation-in-Part of applications Ser. No. 444,622 filed Nov. 26, 1982 and Ser. No. 434,061 filed Oct. 13, 1982.

FIELD OF THE INVENTION

This invention relates to methods for measuring potency of allergenic extracts with increased precision. In particular, this invention relates to procedures for calibrating the potency of allergenic extracts against potency standards so that the extracts can be used with greater precision and reliability in desensitization treatments of patients for allergic reactions.

BACKGROUND OF THE INVENTION

DESCRIPTION OF THE PRIOR ART

Radiometric and fluorometric methods for identifying and measuring allergy specific IgE levels in patient serum are commercially available and are known as the RAST test, for example. U.S. Pat. Nos. RE-29,474; 3,555,143; 3,648,346; 3,720,760 and 3,966,898 relate to these methods and reagents therefor. Enzymatic immunological methods for identifying and quantifying antigens and antibodies in liquids are widely used and are known as the ELISA and EIA tests, for example. Basic technology for enzymatic assays and reagents therefor are disclosed in U.S. Pat. Nos. RE-29,169 and 3,839,153, for example.

A review of the current state of the art with regard to immunoassays for the detection of proteins in solutions is provided by R. Rose et al, *Manual of Clinical Immunology*, 2nd ed. American Society for Microbiology, Washington, pp 327–429, 775–849 (1980) and by A. Voller et al, *Immunoassays for the 80's*, University Park Press, Baltimore (1981), and the publications cited in both of these publications, the entire contents all of which are hereby incorporated by reference. The chapter of *Immunoassays for the 80's*, supra, by T. A. E. Platts-Mills et al, titled "Radio-immunoassays in Allergy", pp 289–311, and the publications cited therein provide a comprehensive review of allergy tests.

Procedures for standardizing allergens are summarized by Rose et al in *Manual of Clinical Immunology*, supra, pp 778–788, and the citations therein. In one RAST approach, allergen of unknown potency is coupled to a solid support, and the quantity required to give a certain degree of reactivity in the RAST test has been determined. In a second approach termed "RAST inhibition", the allergen of unknown potency is incubated with standardized allergen coupled to a solid support and reagent IgE specific to the allergen, and competitive binding occurs. In both procedures, the bound IgE is determined with radiolabeled IgG specific to IgE, and the results are compared to those obtained with the procedure using reference allergens of known potency. Both procedures have limited accuracy, however. Partially because of the wide discrepancies found in tests of the same material (test limitations) and the crude, highly variable extracts of very limited stability usually administered (reagent variability), mandatory potency standards have not yet been adopted by regulatory agencies.

Procedures for binding proteins to insoluble supports have been previously described. Antibodies have been covalently bonded to insoluble supports as described in U.S. Pat. Nos. 3,551,555, 3,553,310, 4,048,298 and RE-29,474. Binding of antibodies to polystyrene by adsorption has been described in U.S. Pat. Nos. 3,646,346 and 4,092,408, for example. Allergens have been covalently bonded to a variety of insoluble supports as described in U.S. Pat. No. 3,720,760.

Polyethylene glycol has been used in protein fractionation processes described by A. Polson et al, *Biochim. Biophys Acta*, vol. 82, pp 463–475 (1964) and A. Polson et al, *Vox Sang*, vol. 23, pp. 107–118 (1972).

SUMMARY OF THE INVENTION

This invention relates to a method for measuring the potency of allergen extracts. It comprises the steps of first contacting an insoluble support having reagent allergen adhered thereto with an aqueous solution containing a known concentration or dilution of the allergen extract and a known amount of IgE specific to allergenic components present in the reagent allergen and presumed present in the allergen extract. The amount of IgE is insufficient to bind with all of the reagent allergen. The contact is maintained for a time sufficient to permit conjugation of IgE with allergenic components. The solution is then removed from the support. The support is then contacted with an aqueous solution of anti-IgE antibody labeled with a fluorogenic enzyme, for sufficient time to permit conjugation of anti-IgE antibody with IgE which has conjugated with reagent allergen on the insoluble support. The term "fluorogenic enzyme", as used herein means an enzyme, in the presence of which, a substrate will release or react to yield a fluorescent product. The solution is then removed from the support. The support is then contacted with an aqueous solution of substrate which undergoes chemical reaction to yield a fluorescent product when in the presence of the fluorogenic enzyme, for sufficient time to yield a fluorescent product. The level of fluorescence in the solution is then measured.

In certain preferred embodiments of this invention, the insoluble support has a plurality of test wells separated by opaque material, the anti-IgE antibody is a monoclonal antibody to which alkaline phosphatase is bound, the anti-IgE is contacted with the insoluble support in an aqueous solution containing from 1 to 8 weight percent polyethylene glycol having a molecular weight of from 1000 to 10,000 and a non-ionic surfactant, and the substrate is 4-methylumbelliferyl phosphate. If the allergen bonded to the insoluble support is covalently bonded to a water-soluble protein having absorption or adsorption affinity for the insoluble support, the insoluble support is preferably prerinsed with an aqueous buffered rinse solution containing from 0.0001 to 0.5 weight percent of the water-soluble protein.

BRIEF DESCRIPTION OF THE DRAWING

The FIGURE is a graph showing inhibition curves for allergens of reference and unknown potencies.

DETAILED DESCRIPTION OF THE INVENTION

Key to successful treatment of allergic conditions is the accurate identification of the offending allergen and the titration of the patient to determine the effective desensitization dosage. In general, reconstituted allergen extract is injected in sufficient quantity to cause major production of antigen-specific IgG (blocking antibody) and major production and/or activation of suppressor T lymphocytes. However, the quantity should not be sufficient to cause major allergic reaction. To the extent that antigen-specific IgE is produced at an increased level, it is critical that the IgG and suppressor IgE production be in such balance as to prevent allergic reaction.

The concentration and amount of the desensitization dosage are dependent upon many factors which are specific to the patient undergoing the allergic reaction. It is, therefore necessary to titrate the patient to determine the proper dosage. A variety of standard titrating techniques are available. Examples of traditional procedures are described in *Remington's Pharmaceutical Sciences*, supra, pp 1344–1352, the entire contents of which are incorporated herein by reference. However, the methods available prior to this invention have lacked the specificity and accuracy to be more than a rough approximation of the order of magnitude of the appropriate beginning dosage range.

Methods providing the specificity and accuracy to determine a suitable desensitization dosage, particularly when the allergen used for desensitization and the allergen component of the diagnostic method have the same allergen profile and specificity have been described in our commonly assigned, copending application Ser. No. 462,585 filed Jan. 31, 1983, the entire contents of which are incorporated by reference. After identification and quantification of the offending allergen, standard desensitization immunotherapy procedures are employed. The procedure normally used involves injecting into the patient gradually increased doses of the allergen, usually to maximum tolerated doses (doses not giving rise to major allergic response), at varying intervals in an attempt to develop IgG antibody protection against the agents and to increase the specific suppressor T lymphocyte activity.

With the method of this invention, the potency of the allergenic extract can be precisely measured, permitting an exact determination of the dosage of extract which should be administered, making unnecessary the exacting procedures formerly required. The exact mechanisms of this treatment are not fully understood. Booster injections to maintain the requisite IgG and suppressor T lymphocyte levels are required at intervals of one to four weeks. Usually the doses required for booster injections are substantially greater than the maximum dose required for control of the initial allergic reaction.

Comparable activity levels of two allergen extracts can be determined by comparing allergen activity levels of serial dilutions of one allergen extract with serial dilutions of the other allergen extract. The comparative dilutions at which one allergen extract has the same potency as the other extract indicate the comparative potencies. This procedure can be carried out using the novel fluorometric inhibition assay method of this invention. If one of the extracts is an allergen extract to be used as a standard for assigning a relative potency, the relative potency expressed as relative dilution required to match the potency of the standard can be determined. Because of the improved accuracy and reproducability provided by the assay of this invention and the availability of highly purified, stable allergens which is the subject of concurrently filed, commonly assigned patent application Ser. No. 476187 AX-19 filed 3-17-83 by Tsay Yuh-geng, Myron A. Beigler, Emanuel Calenoff, Gerald L. Friesen and James L. Nichols, entitled Stable Allergenic Extracts And Methods, it is possible to provide allergens of standardized potencies for diagnostic and therapeutic purposes.

The fluorometric inhibition assay method of this invention comprises a first step of contacting an insoluble support having reagent allergen adhering thereto with an aqueous solution. The solution contains a known concentration or dilution of allergen extract and a known amount of reagent IgE specific to the allergenic components present in the reagent allergen and presumed present in the allergen extract. The amount of reagent IgE is insufficient to bind with all of the reagent allergen. The contact is maintained for a time sufficient to permit conjugation of reagent IgE with allergenic components. The solution is then removed from the support.

The contact or incubation time should be sufficient to permit substantial conjugation to occur between reagent Ige and allergen, the time being temperature dependent. Suitable incubation times are from 30 to 180 minutes at temperatures within the range of from 18° to 40° C., the preferred contact time being from 60 to 120 minutes at temperatures within the range of from 20° to 26° C.

The solution contains an amount of reagent Ige specific to the allergenic components which is insufficient to bind with all of the allergenic components present in the reagent allergen adhering to the insoluble support. Preferably the amount is sufficient to bind from 5 to 20 and optimally from 8 to 10 times the binding capacity of an IgE free control serum. Allergen specific reagent IgE is known in the art and is most conveniently obtained as a serum pool from atopic patients with allergen specific IgE.

The solution preferably contains buffers. The preferred solution has a pH of from 6 to 8 and can be a phosphate buffer solution having a phosphate molarity of from 0.01 to 0.05 and contains from 0.01 to 0.1 weight percent non-ionic surfactant, and from 0.0001 to 0.5 of a non-interfering animal protein.

The insoluble support having the allergen adhering thereto is an important aspect of this invention. The allergen can be any allergenic material such as allergen derived from pollens derived from trees, shrubs, weeds, and grasses; molds; smuts; dusts; allergens derived from danders, hair, and epidermals of animals; extracts derived from insects including insect venoms; and from foods.

A wide variety of compounds can be employed as the solid support, the primary consideration being the binding of the allergens to the surface, the absence of interference with the enzyme labeled anti-IgE antibody reagent, enzymatic reaction thereof with a substrate and fluorescent properties of the enzymatic reaction product. Suitable supports and the coupling of allergens thereto are described in commonly assigned, copending application Ser. No. 462,585 filed Jan. 31, 1983.

A preferred diagnostic support of this invention comprises a polystyrene, styrene copolymers including styrene-(vinyl monomer) copolymers such as styrene-acrylonitrile copolymers, or polyolefins such as polyethylene and polypropylene, and acrylate and methacrylate polymers and copolymers in the form of beads or other surfaces. The allergenic extract is preferably bound thereto by adsorption, ionic bonding, van der Waals adsorption, electrostatic bonding, other non-covalent bonding. It can also be bound to the support by covalent bonding. A particularly advantageous support for this procedure comprises a microtiter plate having a plurality of wells. The well surface or plastic cup inserts therein can constitute the allergen support. Most advantageously, the microtiter plate or the well inserts are opaque to light so that excitation light applied to a well or fluorescence generated in response thereto does not reach or influence contents of the surrounding wells. With this system each well can be employed as a test system independent of the other wells.

Preferably the allergen is covalently bonded to a water-soluble polymer having an affinity for the insoluble substrate. The allergen-polymer product is then adhered to the insoluble substrate by non-covalent bonding such as by adsorption or absorption.

Suitable water-soluble proteins include bovine serum albumins of bovine (BSA), human (HSA), rabbit (RSA), goat (GSA), sheep (SSA), horse (HOSA), etc.; serum gamma Globulin of the previously described animals; and other animal proteins such as ovalbumin, fribrinogen, thrombin, transferin, glycoproteins, etc. Suitable water-soluble amino acid polymers include polylysine, polyglutamic acid, polyalanine, polyhistidine, polymethionine, polyproline, etc. The allergen can be covalently bonded to water-soluble protein or amino acid polymer with conventional coupling agents using methods which are known in the art. Preferably the coupling agent is a carbodiimide such as 1-ethyl-3-(3-N,N-dimethylaminopropyl)carbodiimide hydrochloride and 1-cyclohexyl-3(2-morpholinoethyl)carbodiimide methyl-p-toluenesulfonate. Other suitable coupling agents include aldehyde coupling agents having either ethylenic unsaturation such as acrolein, methacrolin, or 2-butenal or having a plurality of aldehyde groups such as glutaraldehyde, propanedial or butanedial. Other coupling agents include bifunctional NHS-esters such as disuccinimidyl suberate, disuccinimidyl tartarate, bis-[2-(succinimidooxycarbonyloxy)ethyl]sulfone, disuccinimidyl(N,N'-diacetylhomocystine, dithiobis(succinimidyl propionate), ethylene glycolbis(succinimidyl succinate); heterobifunctional reagents such as N-5-azido-2-nitrobenzoyloxy succinimide, p-azidophenacyl bromide, p-azidophenylglyoxal, 4-fluoro-3-nitrophenyl azide, N-hydroxysuccinimidyl-4-azidobenzoate, m-maleimidobenzoyl N-hydroxysuccinimide ester, methyl-4-azidobenzoimidate.HCl, p-nitrophenyl 2-diazo-3,3,3-trifluoropropionate, N-succinimidyl-6(4'-azido-2'-nitrophenylamino)hexanoate, succinimidyl 4-(N-maleimido-methyl)cyclohexane-1-carboxylate, succinimidyl 4-(p-maleimidophenyl)butyrate, N-succinimidyl(4-azidophenyldithio)propionate, N-succinimidyl 3-(2-pyridyldithio)propionate, N-(4-azidophenylthio)phthalimide, homobifunctional reagents such as 1,5-difluoro-2,4-dinitrobenzene, 4,4'-difluoro-3,3'-dinitrodiphenylksulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate; and bifunctional imidoesters such as dimethyl adipimidate.2HCl, dimethyl suberimidate, dimethyl 3,3'-dithiobispropionimidate.2HCl, 2-iminothiolane.HCl. Covalent bonding of allergen to the insoluble protein can be carried out with the above reagents by conventional, well-known reactions, for example in the aqueous solutions at a neutral pH, at temperatures of less than 10° C. for 18 hours or overnight.

In a procedure for non-covalent adhesion of allergen to the surface of an insoluble support, the allergenic material can be applied to the surface of a support such as a polystyrene microtiter well or polystyrene individual insert well therefor, in an aqueous buffer solution. The surface is initially cleaned with a cleaning fluid such as methanol and dried. The buffered allergen solution is placed in the well or insert cup and incubated at room temperature until adsorption occurs, for example for from 2 to 18 hours and preferably from 16-18 hours, at temperatures of from 4° to 40° C. and preferably from 20° to 26° C. The well is then rinsed with a weak saline solution and dried.

Procedures for covalently adhering allergens to insoluble supports are described by Ichiro Chibata in *Immobilized Enzymes*, Halsted Press, New York, 1978, and by A. Cuatrecasas, *J. Bio. Chem.* 245 3059(1970), the entire contents of which are hereby incorporated by reference. The surface can be coated with a protein and coupled with allergen using the procedures described in U.S. Pat. No. 4,210,418 using glutaraldehyde as a coupling agent, for example. In a still further procedure, the well can be coated with a layer having free isocyanate groups such as a polyether isocyanate, and application of the allergen in aqueous solution thereto effects the requisite bonding. In a still further procedure, the allergen can be coupled to a hydroxylated material by means of cyanogen bromide as described in U.S. Pat. No. 3,720,760.

Preferred allergens are those described in commonly assigned copending patent application Ser. No. 433,962 filed Oct. 13, 1982, the entire contents of which are incorporated by reference.

If the allergen is covalently bonded to a water-soluble polymer having an affinity for the insoluble-substrate and the water-soluble polymer has antigenic properties, the first step is preferably preceded by a prerinse step. In the prerinse step, the support surface is contacted with an aqueous buffered rinse solution containing from 0.0001 to 0.5 weight percent of the water-soluble antigenic polymer to which the allergen is bound. This prerinse step is particularly advantageous when the water-soluble polymer is water-soluble animal protein because rinse residue will provide a sufficient amount of the water-soluble protein to conjugate with any of the protein-specific IgE which might be present in the solution.

A preferred rinse solution of this invention is an aqueous phosphate buffer solution having a phosphate molarity of from 0.0001 to 0.05, a pH of from 6 to 8 and containing from 0.001 to 0.1 weight percent non-ionic surfactant and from 0.0001 to 0.5 weight percent of the antigenic protein to which the allergen is coupled. Suitable non-ionic surfactants include polyoxyethylene ethers (BRIJ ®) such as lauryl, cetyl, oleyl, stearyl, and tridecyl polyoxyethylene ethers; polyoxyethylenesorbitans (TWEEN ®) such as polyoxyethylenesorbitan monolaurate, monopalmitate, monostearate, monoleate and trioleates; and other polyoxyethylene ethers (TRITON ®), for example. A preferred non-ionic surfactant is octylphenoxypolyethoxy ethanol having 40 ethylene oxide units (TRITON X-405, Rohm and Haas Company.

The buffer solution is advantageously prepared from a reagent concentrate of the invention comprising from 0.005 to 2.5 weight percent of the animal protein corresponding to the animal protein to which the allergen is covalently bonded, from 0.5 to 5 weight percent nonionic surfactant, from 10 to 20 weight percent sodium chloride, from 0.5 to 5 weight percent stabilizer and sufficient phosphate salt to provide for a 0.02 to 0.05 M phosphate solution. The pH can be from 6 to 8. The preferred buffer concentrate contains about 0.5 weight percent of the animal protein, 0.1 weight percent TRITON X-405 non-ionic surfactant, 17 weight percent sodium chloride, and 2 weight percent sodium azide, 0.01M phosphate and has a pH of 7.4.

After conjugation of reagent IgE with allergen adhering to the insoluble support has occurred, the solution is removed therefrom. Surplus liquid is removed and the solid surface is then rinsed with a suitable rinse solution such as that described above.

The second step of the process of this invention comprises contacting the insoluble support with an anti-Ige antibody labeled with a fluorogenic enzyme. The incubation is continued for sufficient time to permit serum IgE conjugated with allergen (if any) on the insoluble support to conjugate with the anti-IgE antibody. After incubation, the excess liquid is removed, and the surface of the insoluble support is rinsed with a weak saline solution as described above with respect to the first step to remove unconjugated antibody. Preferably the support is rinsed with the preferred rinse solution of this invention described above.

Anti-IgE antibodies are available from many sources, and the methodology for producing them is well known and is described in several of the patents and publications cited above. The preferred antibodies are monoclonal antibodies. The technology for making monoclonal antibodies is well developed, and the procedures suitable for making monoclonal anti-IgE antibodies are described by D. Catty, et al in "Antisera in Immunoassays with special Reference to Monoclonal Antibodies to Human Immunoglobulins", *Immunoassay's for the 80's*, supra, pp 133–153 and the publications cited therein, the entire contents of which are hereby incorporated by reference.

Fluorogenic enzymes (enzymes in the presence of which a substrate will produce a fluorescent product) and methods for bonding enzymes to antibodies without impairing the ability of the antibody to selectively conjugate with antigen are well known in the art. Suitable enzymes and procedures for coupling them to antibodies are described in U.S. Pat. No. 4,190,496, for example, the contents thereof being hereby incorporated by reference. The preferred fluorogenic enzymes and the suitable substrates corresponding thereto include horseradish peroxidase for which a suitable substrate is homovanillic acid or 4-hydroxy-3-methoxyphenylacetic acid, beta-galactosidase for which a suitable substrate is 4-methylumbelliferyl-beta-D-Galactoside, alkaline phosphatase for which a suitable substrate is 4-methylumbelliferyl phosphate and other umbelliferyl phosphates such as 4-carboxyumbellifery phosphate, and umbelliferyl phosphate 4-carboxy alkylesters, etc.

Examples of suitable procedures for enzyme labeling the anti-IgE antibody include the use of carbodiimides, dialdehydes, and bifunctional coupling reagents as described above for covalently bonding allergen to water-soluble proteins such as BSA, for example.

The enzyme labeled anti-IgE antibody is applied to the insoluble support in an aqueous solution. The solution preferably contains suitable salts and buffers to preserve the reactants and facilitate the conjugation reaction. For example, the solution can contain bovine serum albumin (BSA), phosphate buffer solution (PBS), and a mild surfactant such as a polyoxyethylene sorbitan ester employed in the rinse solutions described above. The rinse solutions described herein can also be used.

A preferred solution of this invention comprises from 0.1 micrograms per ml to 5 micrograms per ml and preferably from 1 microgram per ml to 2 microgram per ml anti-IgE antibody in an aqueous phosphate buffered solution having a phosphate molarity of from 0.005 to 0.1 and preferably from 0.0001 to 0.05 and a pH of from 6.0 to 8.0 and preferably 7.2 to 7.6. A critical ingredient in the anti-IgE solution is polyethylene glycol having molecular weights of from 1000 to 8000 and preferably from 2000 to 4000 in concentrations of from 1 to 8 weight percent and preferably from 2 to 6 weight percent. Polyethylene glycols greatly increase the speed and sensitivity of the reaction. Another important ingredient is a non-ionic surfactant in concentrations of from 0.001 to 0.5 and preferably from 0.02 to 0.1 weight percent. Suitable non-ionic surfactants include those described above with respect to rinse solutions, for example. A preferred non-ionic surfactant is TRITON X-405. The surfactant surprisingly reduces the non-specific background fluorescence signal in the assay.

With the preferred anti-IgE solutions of this invention, the incubation time of the solutions with the insoluble support is temperature dependent. At temperatures of 18° to 40° C., incubation times of at least from 30 to 180 minutes can be used. The preferred temperatures are within the range of from 20° to 26° C., and at these temperatures, incubation times from 60 to 120 minutes can be employed. It should be appreciated that prolonged incubation times in any of the steps of this invention can reduce the efficacy of the process. Since rapid analysis is an objective of this invention, the lowest times which still yield the desired accuracy are preferred.

The solid support is then rinsed to remove residual, unconjugated enzyme labeled anti-IgE antibody. The rinse solutions described above are suitable.

The third step of the process of this invention comprises contacting the solid support with a solution of a substrate which undergoes chemical reaction in the presence of the fluorogenic enzyme for a time sufficient for fluorescent compounds to be formed. Suitable substrates and the enzymes they are converted by are known in the art and are described in U.S. Pat. No. 4,190,496, for example. Examples of substrates have been described hereinabove with respect to the corresponding fluorogenic enzyme.

The solid is contacted with an aqueous solution of the substrate containing from $10^{-2}$ to $10^{-10}$ molar and preferably from $10^{-4}$ to $10^{-5}$ molar concentrations of the substrate. Preferred additional reagents and buffers in the substrate solution include 2-amino-2-methyl-1-propanol buffer and magnesium chloride, for example.

The substrate solution is incubated with the insoluble support for sufficient time for the fluorescent reaction product to form. At temperatures of from 18° to 40° C., incubation times of from 5 to 240 minutes can be used. Preferably, the temperature is within the range of from 20° to 26° C., and the incubation time is from 30 to 90 minutes.

The fluorescence level in the solution is then measured. The equipment and procedures for determining the level of fluorescence in the substrate solutions are those conventionally employed in the art. The level of fluorescence is a function of the enzyme concentration on the insoluble support which is, in turn, an inverse function of the amount of allergen in the diluted allergen extract. Suitable fluorometers are the fluorometers by Perkin-Elmer, American Instrument Company, and Turner Designs. The Allergenetics Fluorometer (Allergenetics, Inc., Mountain View, Calif.) is preferred.

In reverse inhibition assay procedures using serial dilution techniques, it is necessary to carry out steps of the method of this invention with two controls in addition to the carrying it out with diluted allergen extracts. For one control, the procedure is repeated without allergen extract to yield a fluorescence reading A, and for the other control, the procedure is again repeated without reagent allergen specific IgE to yield a fluorescence reading a. The percentage (%) of inhibition by each dilution of allergen extract of unknown potency and by each dilution of reference allergen extract of standard potency is then determined from the respective fluorescence readings X.

The percentage (%) of inhibition is calculated from the fluorescent readings obtained according to the following equation:

$$\% \text{ inhibition} = \frac{(A - a) - (X - a)}{A - a} \times 100\%$$

wherein
A is the fluorescence signal obtained in carrying out the procedure described above without any allergen extract,
X is the fluorescence signal obtained with diluted allergen extract, and
a is a blank fluorescence signal obtained in carrying out the procedure described above without any reagent allergen specific IgE.

Inhibition curves are established for the allergen extract of unknown potency and for the reference allergen extract of known or standard potency as shown in the Figure with the percentage (%) of inhibition on the vertical axis and the amount of allergen extract (or dilution factor) on the horizontal axis (logarithymic scale) of logarithymic paper.

To standardize a commercial allergen extract for use for desensitizing patients experiencing allergic reactions, it is preferred to carry out the above-described procedure with both the reference allergen extract and unknown allergen extract. An inhibition curve is established for each extract with the (%) inhibition on the vertical axis and amount of allergen extract or dilution factor on the horizontal axis. By comparing the inhibition curves as illustrated in the Figure, the relative concentrations or dilutions of the allergen extract being standardized and the standard extract necessary to provide the same level of inhibition provides a highly accurate measure of relative (and absolute) potency. The range of concentrations is most advantageously obtained by serial dilution.

This invention is further illustrated by the following specific but non-limiting examples. Temperatures are given in degrees Centigrade.

EXAMPLE 1

To a solution of timothy grass pollen allergen extract (3 mg/ml) was added 10 microliters of a 5 wt/% bovine serum albumin (BSA) solution. After addition, the solution was kept at 4° C., and 5 mg of 1-Ethyl-3-(3-N,N-Dimethylaminopropyl)carbodiimide (ECDI) was added. The mixture was gently stirred at 4° C. for 20 minutes. The additions of both BSA and ECDI were repeated three more times. The final mixture was allowed to stand at 4° C. overnight to yield a conjugate of timothy grass pollen allergen covalently bonded to BSA.

EXAMPLE 2

The procedure of Example 1 was repeated, replacing the timothy grass pollen extract with the following allergenic extracts: Grasses—Bermuda Grass, *Cynodon dactylon*, Orchard Grass, *Dactylis glomerata*, Perennial Rye Grass, *Lolium perenne*, June Grass (Kentucky Blue), *Poa pratensis*, Bent Grass, *Agrostis maritima*, Johnson Grass, *Sorghum halepense*, Brome Grass, *Bromus inermis*, Bahia Grass, *Paspalum notatum*, Corn Grass, *Zea mays*, Meadow Fescue, *Festuca elatior*, and Redtop, *Agrostis alba;* Weeds—Short Ragweed, *Ambrosia artemisifolia*, Western Ragweed; *Ambrosia psilostachya*, False Ragweed, *Franseria acanthicarpa;* Sagebrush (common), *Artemisia tridentata*, Dandelion, *Taraxacum vulgare*, English Plantain, *Plantago lanceolata*, Lamb's Quarters, *Chenopodium album*, Russian Thistle, *Salsola kali*, Goldenrod, *Solidago* sp., Pigweed, *Amaranthus retroflexus*, Dock (yellow), *Rumex crispus*, and Sheep Sorrel, *Rumex acetosella;* Trees—Box Elder (Maple), *Acer negundo*, Alder, *Alnus rhombifolia*, Birch, *Betula nigra*, Mountain Cedar, *Juniperus sabinoides*, White Oak, *Quercus alba*, Elm, *Ulmus americana*, Olive, *Olea europaea*, Black Walnut, *Juglans nigra*, Sycamore, *Platanus occidentalis*, Cottonwood, *Populus trichocarpa*, White Ash, *Fraxinus americana*, White Plain, *Pinus monticola*, Eucalyptus, *Eucalyptus* sp., Acacia, *Acacia baileyana*, Aspen, *Populus tremuloides*, Arizona Cypress, *Cupressus arizonica*, Mesquite, *Prosopis juliflora*, Privet, *Ligustrum ovalifolium*, Melaleuca (Punk Tree), *Melaleuca leucadendron*, and Australian Pine (Beefwood), *Casuarina equisetifolia;* Epidermals—Cat Epithelium, Dog Hair and Dander, Horse Hair and Dander, Cow Hair and Dander, Guinea Pig Hair and Dander, Feather Mix (Chicken, Duck & Goose), and Wool (Sheep); Molds—*Penicillium notatum*, *Cladosporium herbarum*, *Aspergillus fumigatus*, *Mucor racemosus*, *Candida albicans*, and *Alternaria tenuis;* House Dust; Mite—*Dermatophagoides farinae;* and Foods—Milk, Wheat, Corn, Rice, Peanut, Soybean, Shrimp, Tomato, Pork, Carrot, Orange, Potato, Tuna, Beef, Lamb, Chicken, Whole Egg, Yeast (Bakers), Sweet Potato, Cabbage, Lettuce, Pepper (Bell), Apple, Cranberry, Grape, Barley, and Onion. This yielded the corresponding, respective, covalently bonded BSA conjugate of each allergen.

EXAMPLE 3

Repeating the procedure of Example 1 but replacing the timothy grass pollen extracts with extracts of the following tree pollens yields the corresponding, respective covalently bonded BSA-allergen conjugates: Acacia—*Acacia longifolia;* Ailanthus (See Tree of Heaven)—*Ailanthus altissima;* Alder, Mountain (Tag) (Slender)—*ainus tenuifolia/incana;* Alder, Red (Oregon)—*Alnus rubra;* Alder, Sitka—*Alnus sinuata;* Almond—*Prunus amygdalus;* Apple—*Pyrus malus (Malus pumila);* Apricot—*Prunus armeniaca;* Arbor Vitae, Oriental (Ornamental)—*Betula papyrifera;* Birch, Spring—*Betula fontinalis;* Birch, White (Weeping)—*Betula pendula;* Birch, Yellow—*Betula lutea;* Blue Beech (Am. Hornbeam)—*Carpinus carolineana;* Bottle Brush—*Callistemon citrinus;* Butternut—*Juglans cinerea;* Carob Tree—*Ceratonia siliqua;* Cedar, Deodar—*Cedrus deodora;* Cedar, Giant—*Thuja plicata;* Cedar, Incense—*Linocedrus decurrens;* Cedar, Japanese—*Cryptomeria japonica;* Cedar, Port Orford (Lawson Cypress)—*Chamaecyparis lawsoniana;* Cedar, Red—*Juniperus virginiana;* Cedar, Rocky Mountain—*Juniperus scopulorum;* Cedar, Salt (Tamarisk)—*Tamarix gallica;* Cedar, White—*Thuja occidentalis;* Cherry, *Prunus cerasus;* Chestnut, American—*Castanea dentata;* Chestnut, Horse—*Aesculus hippocastanum;* Cottonwood, Common—*Populus deltoides;* Cottonwood, Fremont—*Populus fremontii;* Cypress, Bald (White)—*Taxodium distichum;* Cypress, Italian—*Cupressus sempervirens;* Cypress, Monterey—*Cupressus macrocarpa;* Elderberry—*Sambucus glauca;* Elm, Cedar (Fall Blooming)—*Ulmus crassifolia;* Elm, Chinese—*Ulmus parvifolia;* Elm, Siberian—*Ulmus pumila;* Elm, Slippery—*Ulmus fulva* (rubra); Fir, Douglas—*Pseudotsuga menziesii;* Fir, Red (Noble)—*Abies nobilis* (procera); Fir, White—*Abies concolor;* Gum, Sweet—*Liquidambar styraciflua;* Hackberry—*Celtis occidentalis;* Hazelnut, American—*Corylus americana;* Hemlock, Eastern—*Tsuga canadensis;* Hemlock, Western—*Tsuga heterophylla;* Hickory, Shagbark—*Carya ovata;* Hickory, Shellbark—*Carya laciniosa;* Hickory, White—*Carya tomentosa;* Ironwood (Hop-Hornbeam)—*Ostrya virginiana;* Juniper, California—*Juniperus californica;* Juniper, Chinese—*Juniperus chinensis;* Juniper, Oneseed—*Juniperus monosperma;* Juniper, Pinchot—*Juniperus poinchotti;* Juniper, Utah—*Juniperus osteosperma (juniperus utahensis);* Juniper, Western—*Juniperus occidentalis;* Lilac—*Syringa vulgaris;* Linden (Basswood)—*Tilia americana;* Locust, Black—*Robinia pseudoacacia;* Maple, Big-Leaf (Coast)—*Acer macrophyllum;* Maple, Hard (Sugar)—*Acer saccharum;* Maple, Red—*Acer rubrum;* Maple, Soft (Silver)—*Acer saccharinum;* Mock Orange, Wild (Syringa)—*Philadelphus lewisii;* Mulberry, Paper—*Broussonetia papyifera;* Mulberry, Red—*Morus rubra;* Mulberry, White—*Morus alba;* Oak, Arizona (Gambel)—*Quercus gambelii;* Oak, Arizona Scrub (Canyon)—*Quercus chrysolepsis;* Oak, Black (Yellow)—*Quercus velutina;* Oak, Black Jack—*Quercus marilandica;* Oak, Bur—*Quercus macrocarpa;* Oak, California Black—*Quercus kelloggii*—californica; Oak, California Scrub—*Quercus dumosa;* Oak, Coast Live—*Quercus agrifolia;* Oak, Engelmann—*Quercus engelmanii;* Oak, Garry (Western White)—*Quercus garryana;* Oak, Holly—*Quercus ilex;* Oak, Interior Live—*Quercus wislizenii;* Oak, Post—*Quercus stellata;* Oak, Red—*Quercus rubra;* Oak, Swamp (Pin)—*Quercus palustris;* Oak, Valley—*Quercus lobata;* Oak, Virginia Live—*Quercus virginiana;* Oak, Water—*Quercus nigra;* Olive—*Olea europaea;* Orange—*Citrus sinensis;* Osage Orange—*Maclura pomifera;* Palm, Date—*Phoenix dactylifera;* Palm, Dwarf—*Chamaerops humulis;* Palm, Canary Island Date (Ornamental)—*Phoenix canariensis;* Palm, Queen—*Cocos plumosa;* Peach—*Prunus persica;* Pear—*Pyrus communis;* Pecan—*Carya pecan;* Pepper Tree, California—*Schinus molle;* Pepper Tree, Brazilian—*Schinus terebinthifolius;* Pine, Austrian—*Pinus nigra;* Pine, Canary Island—*Pinus canariensis;* Pine, Digger—*Pinus sabiniana;* Pine, Loblolly—*Pinus taeda;* Pine, Lodgepole—*Pinus contorta;* Pine, Monterey—*Pinus radiata;* Pine, Pinyon—*Pinus edulis;* Pine, Red (Norway)—*Pinus resinosa;* Pine Shortleaf—*Pinus echinata;* Pine, Virginia Scrub—*Pinus, virginiana;* Pine, Western Yellow (Ponderosa)—*Pinus ponderosa;* Pine, White (Eastern)—*Pinus strobus;* Plum (Prune)—*Prunus domestica;* Poplar, Balsam—*Populus balsamifera;* Poplar, Lombardy—*Populus nigra-italica;* Western Balsam (See Cottonwood, Black) *Populus trichocarpa;* Poplar, White—*Populus alba;* Privet—*Ligustrum spp.;* Redwood—*Sequoia sempervirens;* Russian Olive—*Elaeagnus angustifolia;* Spruce, Red—*Picea rubens;* Spruce, Sitka—*Picea stitchensis;* Sycamore, Mapleleaf—*Platanus acerifolia;* Sycamore, Western—*Platanus racemosa;* Tamarack (Larch)—*Larix occidentalis;* Tamarisk (See Cedar, Salt)—*Tamarix gallica;* Tree of Heaven—*Ailanthus altissima;* Walnut, Arizona—*Juglans rupestris;* Walnut, Hind's California Black—*Juglans hindsii;* Walnut, So. California Black—*Juglans californica;* Walnut, English—*Juglans regia;* Willow, Arroyo—*Salix lasiolepis;* Willow, Black—*Salix nigra;* Willow, Pussy—*Salix discolor;* Willow, Red—*Salix laevigata;* Willow, Yellow—*Salix lasiandra.*

EXAMPLE 4

Repeating the procedure of Example 1 but replacing the timothy grass pollen extract with extracts of the following grass and weed pollens yields the corresponding, respective covalently bonded BSA-allergen conjugates: Barley, Cultivated—*Hordeum vulgare;* Bluegrass, Annual—*Poa annua;* Bluegrass, Canada—*Poa compressa;* Bluegrass, Sandberg—*Poa sandbergii;* Brome Broncho-Ripgut—*Bromus rigidus;* Brome, California—*Bronus carinatus;* Brome, Cheat—*Bromus secalinus;* Brome, Soft Cheat—*Bromus mollis;* Bunch, Blue (Northwestern Bunch)—*Agropyron spicatum;* Canarygrass—*Phalaris canariensis;* Canarygrass, Reed—*Phalaris arundinacea;* Fescue, Red—*Festuca rubra;* Grama Grass, Blue (Side Oats)—*Bouteloua gracilis;* Koeler's Grass (Western Junegrass)—*Koeleria cristata;* Lovegrass, Hawaiian—*Eragrostis variabilis;* Oats, Common Cultivated—*Avena sativa;* Oatgrass, Tall—*Avena elatior (Arrhenatherum elatius);* Quack Grass—*Agropyron repens;* Rye, Cultivated—*Secale cereale;* Ryegrass, Alkali—*Elymus triticoides;* Ryegrass, Giant Wild—*Elymus cinereus;* Ryegrass, Italian—*Lolium multiflorum;* Ryegrass, Western—*Elymus glaucus;* Salt Grass—*Distichlis stricta;* Sorghum, Common Cultivated—*Sorghum vulgare;* Sudan Grass—*Sorghum vulgare var. sudanese;* Sweet Vernal grass—*Anthoxanthum odoratum;* Velvetgrass—*Holcus Ianatus;* Wheat, Cultivated—*Triticum aestivum;* Wheatgrass, Crested—*Agropyron cristatum;* Wheatgrass, Western—*Agropyron smithii;* Alfalfa—*Medicago sativa;* Aster—*Aster sinensis;* Balsam Root—*Balsamorhiza sagittata;* Bassia—*Bassia hyssopifolia;* Beach Bur—*Franseria bipinnatifida;* Burro Brush (Greasebush)—*Hymenoclea salsola;* Careless Weed—*Amaranthus palmeri;* Castor Bean—*Ricinus communis;* Cattail, Broadleaf—*Typha latifolia;* Clover, Red—*Trifolium pratense;* Clover, Red—*Trifolium pratense;* Clover, Sweet, Yellow—*Melilotus officinalis;* Clover, White (Dutch)—*Trifolium repens* (album); Cocklebur, Common—*Xanthium strumarium;* Cocklebur, Spiny—*Xanthium spinosum;* Cosmos—*Cosmos bipinnatus;* Daffodil—*Narcissus pseudo-narcissus;* Dahlia—*Dahlia pinnata x coccinea;* Daisy/Chrysanthemum (Oxeyed Daisy)—*Chrysanthemum leucanthemum;* Dock, Bitter—*Rumex obtusifolius;* Dog Fennel (Mayweed)—*Anthemix cotula;* Fireweed, Alaska—*Epilobium angustifolium;* Gladiolus—*Gladiolus Xhortulanus;* Greasewood—*Sarcobatus vermiculatus;* Hemp—*Cannabis sativa;* Hops—*Humulus lupulus;* Hopsage—*Grayia* spinosa; Iodine Bush (Burro Weed)—*Allenrolfea occidentalis;* Kochia (Mex. Firebush)—*Kochia scoparia;* Lily, Easter—*Lilium longiflorum;* Marigold—*Tagetes patula;* Marshelder, Burweed (Giant Poverty)—*Iva Xanthifolia;* Marshelder, Narrowleaf (August)—*Iva angustifolia;* Marshelder, True (Rough)—*Iva ciliata;* Mexican Tea—*Chenopodium ambrosioides;* Mustard, Black—*Brassica nigra;* Mustard, Common Yellow—*Brassica campestris;* Nettle—*Urtica dioica (gracilis)*; Pickleweed—*Salicornia ambigua;* Pigweed, Spiny—*Amaranthus spinosus;* Poppy, California—*Eschoscholzia californica;* Povertyweed, Small—*Iva axillaris;* Rabbit Brush—*Chryso—thamnus nauseosus;* Rabbit Bush (Bur Ragweed)—*Franseria deltoides;* Ragweed, Canyon—*Franseria ambrosioides;* Ragweed, Desert—*Franseria dumosa;* Ragweed, Giant—*Ambrosia trifida;* Ragweed, Silver—*Dicoria canescens;* Ragweed, Slender—*Franseria tenuifolia;* Ragweed, Southern—*Ambrosia bidentata;* Rose—*Rosa multiflora;* Sagebrush—Annual—*Artemisia annua;* Sagebrush, Coast—*Artemisia californica;* Sagebrush, Green (Tarragon)—*Artemisia dracunculus;* Sagebrush, Mugwort—*Artemisia vulgaris heterophylla;* Sagebrush, Pasture (Carpet)—*Artemisi frigida;* Sagebrush, Sand Dune—*Artemisia pycnocephala;* Sagebrush, White (Prairie)—*Artemisia Iudoviciana;* Saltbush, Annual—*Atriplex wrightii;* Scale, All—*Atriplex polycarpa;* Scale, Bract—*Atriplex serenana bracteosa;* Scale, Brewers—*Atriplex lentiformis breweri;* Scale, Lens—*Atriplex lentiformis;* Scale, Red—*Atriplex rosea;* Scale, Silver (Fogweed)—*Atriplex argentea expansa;* Scale, Spear—*Atriplex patula hastata;* Scale, Wing (Shad)—*Atriplex canescen;* Scotch Broom—*Cytisus scoparius;* Sea Blite, California—*Suaeda californica;* Sedge—*Carex barbara;* Sheep Fat—*Atriplex confertifolia;* Snapdragon—*Antirrhinum majus;* Suaeda (See Sea Blite); Sugar Beet—*Beta vulgaris;* Sunflower—*Helianthus annuus;* Waterhemp, Western—*Acnida tamariscina;* Winter Fat—*Eurotia lanata;* Wormseed (Jerusalem Oak)—*Chenopodium, botrys;* Wormwood, Absinthe—*Artemisia absinthium.*

EXAMPLE 5

Repeating the procedure of Example 1 but replacing the timothy grass pollen extract with extracts of the following epidermals and glandular extracts yields the corresponding covalently bonded BSA-allergen conjugates: Camel Hair & Dander; Deer Hair & Dander; Feathers, Parakeet; Feathers, Pigeon; Feathers, Turkey; Fox Fur; Gerbil Hair & Epithelium; Glue, Fish; Goat Hair & Dander; Hamster Hair & Epithelium; Hog Hair & Dander; Human Hair; Mink Fur; Mohair; Monkey Hair & Epithelium; Mouse Hair & Epithelium; Poodle Hair & Dander; Pyrethrum; Rabbit Hair & Epithelium; Rat Hair & Epithelium; Seal Fur; Wool, Sheep.

EXAMPLE 6

Repeating the procedure of Example 1 but replacing the timothy grass pollen extract with extracts of the following dusts yields the corresponding respective covalently bonded BSA-allergen conjugates: Acacia Gum; Alfalfa Hay; Algae, Chlorella spp.; Carragheen Gum; Coconut Fiber; Cotton Linters; Cottonseed; Dust, Barley; Dust, Corn; Dust, Grain Mill; Dust, Mattress; Dust, Oat; Dust, Pea; Dust, Rye; Dust, Soybean; Dust, Upholstery; Dust, Wheat; Dust, Wood—Cedar/-Juniper; Dust, Wood—fir/Hemlock; Dust, Wood—Gum; Dust, Wood—Mahogany; Dust, Wood—Maple; Dust, Wood—Oak Mix; Dust, Wood—Pine Mix; Dust, Wood—Redwood; Dust, Wood—Spruce; Dust, Wood—Walnut; Fern Spores, sp.; Flax Fiber; Flaxseed; Hemp; Jute; Kapok; karaya Gum; Lycopodium; Orris Root; Paper Mix; Pyrethrum; Silk; Sisal; Tragacanth Gum; Timothy Hay; Tobacco, Pipe; Tobacco, Cigarette; Tobacco, Cigar; Tobacco, Leaf.

EXAMPLE 7

Repeating the procedure of Example 1 but replacing the timothy grass pollen extract with extracts of the following foods yields the corresponding respective covalently bonded BSA-allergen conjugates: Allspice; Almond; Apricot, Food; Arrowroot; Artichoke; Asparagus; Avocado; Banana; Bay Leaf; Bean, Kidney; Bean, Lima; Bean, Navy; Bean, Pinto-Frijole; Bean, String-/Wax; Beet; Black-Eyed Pea; Blueberry; Brazil Nut; Buckwheat; Cashew Nut; Celery; Cheese, Cheddar (American); Cheese, Parmesan; Cheese, Roquefort; Cheese, Swiss; Cherry Mix; Chewing Gum Base; chicken; Chicory; Chili Pepper; Chocolate/Cocoa; Cinnamon; Clam; Cloves; Cola; Coconut; Codfish Mix; Coffee; Crab; Cucumber; Curry Powder; Date; Dill; Egg White; Egg, Yolk; Eggplant; Endive; Garlic; Gelatine; Ginger; Raisin Mix; Grapefruit; Haddock; Halibut; Hazelnut (Filbert) Herring; Honey; Hops Food; Horseradish; Lamb; Lemon; Lentil; Lime; Liver; Beef (Calves); Lobster; Mackerel; Malt; Mangoes; Maple, Syrup/Sugar; Melon, (see Muskmelon Mix); Milk, Cow's (Albumin); Milk, Cow's (Casein); Milk, Cow's (Whey); Milk, (Evaporated); Milk, Goat's; Mint Mix (Peppermint/Spearmint); Mushroom; Mustard; Nutmeg; Oat, Whole (Grain); Okra; Olive Mix; Onion; Orange, Mandarin/Tangerine; Oregano; Oyster Mix; Papaya; Paprika; Parsley; Parsnip; Pea; Peach Food; Pear Food; Pecan Food; Pepper, Black/-White; Pepper, Bell (Green/Red); Perch, Lake; Pineapple; Plum/-Prune Mix; Poppy Seed; Pumpkin; Rabbit Meat; Radish; Raspberry; Snapper; Rhubarb; Rice, Wild; Rye, Whole (Grain); Safflower Seed; Sage; Salmon; Scallops; Sesame Seed; Sole; Spinach; Squash, Mix; Strawberry; Sugar (Beet); Sugar (Cane); Sunflower Seeds; Tapioca; Tea; Thyme; Trout; Turkey; Turnip; Vanilla; Walnut Food, Black; Walnut Food, English; Watermelon; Whitefish; Yeast, Brewers; Yeast Mix (Bakers/-Brewers, Sacchoromyces cerevisiae).

EXAMPLE 8

Repeating the procedure of Example 1 but replacing the timothy grass pollen extract with extracts of the following molds yields the corresponding respective covalently bonded BSA-allergen conjugates: *Aspergillus clavatus; Aspergillus glaucus; Aspergillus nidulans; Aspergillus niger; Aspergillus restrictus; Aspergillus sydowi; Aspergillus terreus; Botrytis cinerea; Cephalosporium acremonium; Cephalothecium* (*Trichothecium*) *reseum; Chaetomium globosum; Cryptococcus terreus; Cunninghamella elegans; Curvularia spicifera; Dematium nigrum; Epicoccum nigrum; Epidermophyton floccosum; Fomes rimosus; Fusarium vasinfectum; Geotrichum candidum; Helminthosporium maydis; Helminthosporium; Hormodendrum* (*Cladosporium*); *Monilia sitophila; Mycogone* sp.; *Neurospora crassa; Nigrospora sphaerica; Oidiodendrum* sp.; *Paecilomyces varioti; Penicillium artramentosium; Penicillium biforme; Penicillium carminoviolaceum; Penicillium chrysogenum; Penicillium digitatum; Penicillium expansum; Penicillium glaucum; Penicillium intricatum; Penicillium luteum; Penicillium roqueforti; Penicillium roseum; Phoma herbarum; Pleospora* sp.;

*Poria* sp.; *Pullularia pullulans; Rhizopus nigricans; Rhodotorula glutinis; Saccharomyces cerevisiae* (See Yeast Mix); *Scopulariopsis brevicaulis; Spondylocladium* sp.; *Sporobolomyces salmonicolor; Stemphylium botryosum; Streptomyces griseus; Trichoderma viride; Typhula idahoensis; Verticillum alboatrum.*

EXAMPLE 9

Repeating the procedure of Example 1 but replacing the timothy grass pollen extract with extracts of the following smuts yields the corresponding respective covalently bonded BSA-allergen conjugates: Smut, Barley; Smut, Bermuda; Smut Corn; Smut, Johnson; Smut, Oat; Smut, Sorghum; Smut, Wheat.

EXAMPLE 10

Repeating the procedure of Example 1 but replacing the timothy grass pollen extract with extracts of the following insects and insect venoms yields the corresponding covalently bonded BSA-allergen conjugates: Ants, (Black and Red); Ants, Carpenter; Ants, Fire; Aphid; Bee, Bumble; Bee, Honey; Blackfly; Butterfly; Caddis Fly; Cricket; Cockroach Mix; Deer Fly; Flea antigen; Fruit Flies; Gnat sp.; Horney, Black and Yellow; Horse Fly; House Fly; Mayfly sp.; Mite (D. farinae); Mosquito Mix; Moth, Miller; Wasp; Yellow Jacket; Honey Bee Venom Protein—Apis mellifera; Wasp Venom Protein—*Polistes* sp.; White-faced Horner Venom Protein—*Dolichovespula maculata;* Yellow Hornet Venom Protein—*Dolichlovespula arenaria;* Yellow Jacket Venom Protein—*Vespula* sp.; Mixed Vespid Venom Protein.

EXAMPLE 11

The timothy grass pollen allergens-conjugate with BSA prepared in Example 1 was diluted in phosphate buffer, pH 8.5. To each microtiter well was added precisely 100 microliters of the diluted conjugate solution. The coating process was allowed to proceed at room temperature for 2 hours (or overnight). At the end of the coating process, the liquid in each well was removed by aspiration. The wells were washed three times (3×200 microliters) with a phosphate washing buffer containing sorbitol and TRITON ×405. The wells thus coated can be used for assaying patient serum for timothy grass pollen allergen specific IgE antibodies.

EXAMPLE 12

The procedure of Example 11 was repeated but replacing the timothy grass pollen extract—BSA conjugate with the BSA conjugate products of Example 2. This yielded microtiter wells each having adhered thereto a BSA-allergen extract conjugate of: Grasses—Bermuda Grass, Cynodon dactylon, Orchard Grass, *Dactylis glomerata,* Perennial Rye Grass, *Lolium perenne,* June Grass (Kentucky Blue), *Poa pratensis,* Bent Grass, *Agrostis maritima,* Johnson Grass, *Sorghum halepense,* Brome Grass, *Bromos inermis* Bahia Grass, *Paspalum notatum,* Corn Grass, Zea mays, Meadow Fescue, *Festuca elatior,* and Redtop, *Agrostis alba;* Weeds—Short Ragweed, *Ambrosia artemisifolia,* Western Ragweed, *Ambrosia psilostachya,* False Ragweed, *Franseria acanthicarpa,* Sagebrush (common), *Artemisia tridentata,* Dandelion, *Taraxacum vulgare,* English Plantain, *Plantago lanceolata,* Lamb's Quarters, *Chenopodium album,* Russian Thistle, Salsola kali, Goldenrod, Solidago sp., Pigweed, *Amaranthus retroflexus,* Dock (yellow), *Rumex crispus,* and Sheep Sorrel, *Rumex acetosella;* Trees—Box Elder (Maple), *Acer negundo,* Alder, *Alnus rhombifolia,* Birch, *Betula nigra,* Mountain Cedar, *Juniperus sabinoides,* White Oak, *Quercus alba,* Elm, *Ulmus americana,* Olive, *Olea europaea,* Black Walnut, *Juglans nigra,* Sycamore, *Platanus occidentalis,* Cottonwood, *Populus trichocarpa,* White Ash, *Fraxinus americana,* White Pine, *Pinus monticola,* Eucalyptus, *Eucalyptus* sp., Acacia, *Acacia baileyana,* Aspen, *Populus tremuloides,* Arizona Cypress, *Cupressus arizonica,* Mesquite, *Prosopis juliflora,* Privet, *Ligustrum ovalifolium,* Melaleuca (Punk Tree), *Melaleuca leucadendron,* and Australian Pine (Beefwood), *Casuarina equisetifolia;* Epidermals—Cat Epithelium, Dog Hair and Dander; Horse Hair and Dander, Cow Hair and Dander, Guinea Pig Hair and Dander, Feather Mix (Chicken, Duck & Goose), and Wool (Sheep); Molds—*Penicillium notatum, Cladosporium herbarum, Aspergillus fumigatus, Mucor racemosus, Candida albicans,* and *Alternaria tenuis;* House Dust; Mite—*Dermatophagoides farinae;* and Foods—Milk, Wheat, Corn, Rice, Peanut, Soybean, Shrimp, Tomato, Pork, Carrot, Orange, Potato, Tuna, Beef, Lamb, Chicken, Whole Egg, Yeast (Bakers), Sweet Potato, Cabbage, Lettuce, Pepper (Bell), Apple, Cranberry, Grape, Barley, and Onion.

EXAMPLE 13

Repeating the procedure of Example 11 but replacing the timothy grass pollen extract—BSA conjugate with the BSA conjugate products of Example 3 yields microtiter wells each having adhered thereto a BSA-allergen extract conjugate of: Acacia—*Acacia longifolia; Ailanthus* (See Tree of Heaven)—*Ailanthus altissima;* Alder, Mountain (Tag) (Slender)—*ainus tenuifolia/incana;* Alder, Red (Oregon)—*Alnus rubra;* Alder, Sitka—*Alnus sinuata;* Almond—*Prunus amygdalus;* Apple—*Pyrus malus* (*Malus pumila*); Apricot—*Prunus armeniaca;* Arbor Vitae, Oriental (Ornamental)—*Betula papyrifera;* Birch, Spring—*Betula fontinalis;* Birch, White (Weeping)—*Betula pendula;* Birch, Yellow—*Betula lutea;* Blue Beech (Am. Hornbeam)—*Carpinus carolineana;* Bottle Brush—*Callistemon citrinus;* Butternut—*Juglans cinerea;* Carob Tree—*Ceratonia siliqua;* Cedar, Deodar—*Cedrus deodora;* Cedar, Giant—*Thuja plicata;* Cedar, Incense—*Linocedrus decurrens;* Cedar, Japanese—*Cryptomeria japonica;* Cedar, Port Orford (Lawson Cypress)—*Chamaecyparis lawsoniana;* Cedar, Red—*Juniperus virginiana;* Cedar, Rocky Mountain—*Juniperus scopulorum;* Cedar, Salt (Tamarisk-)—*Tamarix gallica;* Cedar, White—*Thuja occidentalis;* Cherry, Prunus cerasus; Chestnut, American—*Castanea dentata;* Chestnut, Horse—*Aesculus hippocastanum;* Cottonwood, Common—*Populus deltoides;* Cottonwood, Fremont—*Populus fremontii;* Cypress, Bald (White)—*Taxodium distichum;* Cypress, Italian—*Cupressus sempervirens;* Cypress, Monterey—*Cupressus macrocarpa;* Elderberry—*Sambucus glauca;* Elm, Cedar (Fall Blooming)—*Ulmus crassifolia;* Elm, Chinese—*Ulmus parvifolia;* Elm, Siberian—*Ulmus pumila;* Elm, Slippery—*Ulmus fulva* (rubra); Fir, Douglas—*Pseudotsuga menziesii;* Fir, Red (Noble)—*Abies nobilis* (procera); Fir, White—*Abies concolor;* Gum, Sweet—*Liquidambar styraciflua;* Hackberry—*Celtis occidentalis;* Hazelnut, American—*Corylus americana;* Hemlock, Eastern—*Tsuga canadensis;* Hemlock, Western—*Tsuga heterophylla;* Hickory, Shagbark—*Carya ovata;* Hickory, Shellbark—*Carya laciniosa;* Hickory, White—*Carya tomentosa;* Ironwood (Hop-Hornbeam)—*Ostrya virgini-* ana; Juniper, California—*Juniperus californica;* Juniper, Chinese—*Juniperus chinensis;* Juniper, Oneseed—*Juniperus monosperma;* Juniper, Pinchot—*Juniperus pinchotti;* Juniper, Utah—*Juniperus osteosperma (juniperus utahensis);* Juniper, Western—*Juniperus occidentalis;* Lilac—*Syringa vulgaris;* Linden (Basswood)—*Tilia americana;* Locust, Black—*Robinia pseudoacacia;* Maple, Big-Leaf (Coast)—*Acer macrophyllum;* Maple, Hard (Sugar)—*Acer saccharum;* Maple, Red—*Acer rubrum;* Maple, Soft (Silver)—*Acer saccharinum;* Mock Orange, Wild (Syringa)—*Philadelphus lewisii;* Mulberry, Paper—*Broussonetia papyifera;* Mulberry, Red—*Morus rubra;* Mulberry, White—*Morus alba;* Oak, Arizona (Gambel)—*Quercus gambelii;* Oak, Arizona Scrub (Canyon)—*Quercus chrysolepsis;* Oak, Black (Yellow)—*Quercus velutina;* Oak, Black Jack—*Quercus marilandica;* Oak, Bur—*Quercus macrocarpa;* Oak, California Black—*Quercus kelloggii-californica;* Oak, California Scrub—*Quercus dumosa;* Oak, Coast Live—*Quercus agrifolia;* Oak, Engelmann—*Quercus engelmanii;* Oak, Garry (Western White)—*Quercus garryana;* Oak, Holly—*Quercus ilex;* Oak, Interior Live—*Quercus wislizenii;* Oak, Post—*Quercus stellata;* Oak, Red—*Quercus rubra;* Oak, Swamp (Pin-)—*Quercus palustris;* Oak, Valley—*Quercus lobata;* Oak, Virgina Live—*Quercus virginiana;* Oak, Water—*Quercus nigra;* Olive—*Olea europaea;* Orange—*Citrus sinensis;* Osage Orange—*Maclura pomifera;* Palm, Date—*Phoenix dactylifera;* Palm, Dwarf—*Chamaerops humulis;* Palm, Canary Island Date (Ornamental)—*Phoenix canariensis;* Palm, Queen—*Cocos plumosa;* Peach—*Prunus persica;* Pear—*Pyrus communis;* Pecan—*Carya pecan;* Pepper Tree, California—*Schinus molle;* Pepper Tree, Brazilian—*Schinus terebinthifolius;* Pine, Austrian—*Pinus nigra;* Pine, Canary Island—*Pinus canariensis;* Pine, Digger—*Pinus sabiniana;* Pine, Loblolly—*Pinus taeda;* Pine, Lodgepole—*Pinus contorta;* Pine, Monterey—*Pinus radiata;* Pine, Pinyon—*Pinus edulis;* Pine, Red (Norway)—*Pinus resinosa;* Pine, Shortleaf—*Pinus echinata;* Pine, Virginia Scrub—*Pinus virginiana;* Pine, Western Yellow (Ponderosa)—*Pinus ponderosa;* Pine, White (Eastern)—*Pinus strobus;* Plum (Prune)—*Prunus domestica;* Poplar, Balsam—*Populus balsamifera;* Poplar, Lombardy—*Populus nigra-italica;* Western Balsam (See Cottonwood, Black) *Populus trichocarpa;* Poplar, White—*Populus alba;* Privet—*Ligustrum spp.;* Redwood—*Sequoia sempervirens;* Russian Olive—*Elaeagnus angustifolia;* Spruce, Red—*Picea rubens;* Spruce, Sitka—*Picea sitchensis;* Sycamore, Mapleleaf—*Platanus acerifolia;* Sycamore, Western—*Platanus racemosa;* Tamarack (Larch)—*Larix occidentalis;* Tamarisk (See Cedar, Salt)—*Tamarix gallica;* Tree of Heaven—*Ailanthus altissima;* Walnut, Arizona—*Juglans rupestris;* Walnut, Hind's California Black—*Juglans hindsii;* Walnut, So. California Black—*Juglans californica;* Walnut, English—*Juglans regia;* Willow, Arroyo—*Salix lasiolepis;* Willow, Black—*Salix nigra;* Willow, Pussy—*Salix discolor;* Willow, Red—*Salix laevigata;* Willow, Yellow—*Salix lasiandra.*

EXAMPLE 14

Repeating the procedure of Example 11 but replacing the timothy grass pollen extract—BSA conjugate with the BSA conjugate products of Example 4 yields microtiter wells each having adhered thereto a BSA-allergen extract conjugate of Barley, Cultivated—*Hordeum vulgare;* Bluegrass, Annual—*Poa annua;* Bluegrass, Canada—*Poa compressa;* Bluegrass, Sandberg—*Poa sandbergii;* Brome Broncho-Ripgut—*Bromos rigidus;* Brome, California—*Bromus carinatus;* Brome, Cheat—*Bromos secalinus;* Brome, Soft Cheat—*Bromus mollis;* Bunch, Blue (Northwestern Bunch)—*Agropyron spicatum;* Canarygrass—*Phalaris canariensis;* Canarygrass, Reed—*Phalaris arundinacea;* Fescue, Red—*Festuca rubra;* Grama Grass, Blue (Side Oats)—*Bouteloua gracilis;* Koeler's Grass (Western Junegrass)—*Koeleria cristata;* Lovegrass, Hawaiian—*Eragrostis variabilis;* Oats, Common Cultivated—*Avena sativa;* Oatgrass, Tall—*Avena elatior (Arrhenatherum elatius);* Quack Grass—*Agropyron repens;* Rye, Cultivated—*Secale cereale;* Ryegrass, Alkali—*Elymus triticoides;* Ryegrass, Giant Wild—*Elymus cinereus;* Ryegrass, Italian—*Lolium multiflorum;* Ryegrass, Western—*Elymus glaucus;* Salt Grass—*Distichlis stricta;* Sorghum, Common Cultivated—*Sorghum vulgare;* Sudan Grass—*Sorghum vulgare* var. sudanese; Sweet Vernal grass—*Anthoxanthum odoratum;* Velvetgrass—*Holcus lanatus;* Wheat, Cultivated—*Triticum aestivum;* Wheatgrass, Crested—*Agropyron cristatum;* Wheatgrass, Western—*Agropyron smithii;* Alfalfa—*Medicago sativa;* Aster—*Aster sinensis;* Balsam Root—*Balsamorhiza sagittata;* Bassia—*Bassia hyssopifolia;* Beach Bur—*Franseria bipinnatifida;* Burro Brush (Greasebush)—*Hymenoclea salsola;* Careless Weed—*Amaranthus palmeri;* Castor Bean—*Ricinus communis;* Cattail, Broadleaf—*Typha latifolia;* Clover, Red—*Trifolium pratense;* Clover, Sweet, Yellow—*Melilotus officinalis;* Clover, White (Dutch)—*Trifolium repens* (album); Cocklebur, Common—*Xanthium strumarium;* Cocklebur, Spiny—*Xanthium spinosum;* Cosmos—*Cosmos bipinnatus;* Daffodil—*Narcissus pseudo-narcissus;* Dahlia—*Dahlia pinnata x coccinea;* Daisy/Chrysanthemum (Oxeyed Daisy)—*Chrysanthemum leucanthemum;* Dock, Bitter—*Rumex obtusifolius;* Dog Fennel (Mayweed)—*Anthemix cotula;* Fireweed, Alaska—*Epilobium angustifolium;* Gladiolus—*Gladiolus Xhortulanus;* Greasewood—*Sarcobatus vermiculatus;* Hemp—*Cannabis sativa;* Hops—*Humulus lupulus;* Hopsage—*Grayia spinosa;* Iodine Bush (Burro Weed)—*Allenrolfea occidentalis;* Kochia (Mex. Firebush)—*Kochia scoparia;* Lily, Easter—*Lilium longiflorum;* Marigold—*Tagetes patula;* Marshelder, Burweed (Giant Poverty)—*Iva Xanthifolia;* Marshelder, Narrowleaf (August)—*Iva angustifolia;* Marshelder, True (Rough)—*Iva ciliata;* Mexican Tea—*Chenopodium ambrosioides;* Mustard, Black—*Brassica nigra;* Mustard, Common Yellow—*Brassica campestris;* Nettle—*Urtica dioica* (gracilis); Pickleweed—*Salicornia ambigua;* Pigweed, Spiny—*Amaranthus spinosus;* Poppy, California—*Eschoscholzia californica;* Povertyweed, Small—*Iva axillaris;* Rabbit Brush—*Chryso-thamnus nauseosus;* Rabbit Bush (Bur Ragweed)—*Franseria deltoides;* Ragweed, Canyon—*Franseria ambrosioides;* Ragweed, Desert—*Franseria dumosa;* Ragweed, Giant—*Ambrosia trifida;* Ragweed, Silver—*Dicoria canescens;* Ragweed, Slender—*Franseria tenuifolia;* Ragweed, Southern—*Ambrosia bidentata;* Rose—*Rosa multiflora;* Sagebrush-Annual—*Artemisia annua;* Sagebrush, Coast—*Artemisia californica;* Sagebrush, Green (Tarragon)—*Artemisia dracunculus;* Sagebrush, Mugwort—*Artemisia vulgaris heterophylla;* Sagebrush, Pasture (Carpet)—*Artemisi frigida;* Sagebrush, Sand Dune—*Artemisia pycnocephala;* Sagebrush, White (Prairie)—*Artemisia ludoviciana;* Saltbush, Annual—*Atriplex wrightii;* Scale, All—*Atriplex polycarpa;* Scale, Bract—*Atriplex serenana bracteosa;* Scale, Brewers—*Atriplex lentiformis breweri;* Scale, Lens—*Atriplex lentiformis;* Scale, Red—*Atriplex rosea;* Scale, Silver (Fogweed)—*Atriplex argentea expansa;* Scale, Spear—*Atriplex patula hastata;* Scale, Wing (Shad)—*Atriplex canescen;* Scotch Broom—*Cytisus scoparius;* Sea Blite, California—*Suaeda californica;* Sedge—*Carex barbara;* Sheep Fat—*Atriplex confertifolia;* Snapdragon—*Antirrhinum majus;* Suaeda (See Sea Blite); Sugar Beet—*Beta vulgaris;* Sunflower—*Helianthus annuus;* Waterhemp, Western—*Acnida tamariscina;* Winter Fat—*Eurotia lanata;* Wormseed (Jerusalem Oak)—*Chenopodium botrys;* Wormwood, Absinthe—*Artemisia absinthium.*

EXAMPLE 15

Repeating the procedure of Example 11 but replacing the timothy grass pollen extract—BSA conjugate with the BSA conjugate products of Example 5 yields microtiter wells each having adhered thereto a BSA-allergen extract conjugate of Camel Hair & Dander; Deer Hair & Dander; Feathers, Parakeet; Feathers, Pigeon; Feathers, Turkey; Fox Fur; Gerbil Hair & Epithelium; Glue, Fish; Goat Hair & Dander; Hamster Hair & Epithelium; Hog Hair & Dander; Human Hair; Mink Fur; Mohair; Monkey Hair & Epithelium; Mouse Hair & Epithelium; Poodle Hair & Dander; Pyrethrum; Rabbit Hair & Epithelium; Rat Hair & Epithelium; Seal Fur; Wool, Sheep.

EXAMPLE 16

Repeating the procedure of Example 11 but replacing the timothy grass pollen extract—BSA conjugate with the BSA conjugate products of Example 6 yields microtiter wells each having adhered thereto a BSA-allergen extract conjugate of Acacia Gum; Alfalfa Hay; Algae, Chlorella-spp.; Carragheen Gum; Coconut Fiber, Cotton Linters; Cottonseed; Dust, Barley; Dust, Corn; Dust, Grain Mill; Dust, Mattress; Dust, Oat; Dust, Pea; Dust, Rye; Dust, Soybean; Dust, Upholstery; Dust, Wheat; Dust, Wood—Cedar/Juniper; Dust, Wood—fir/Hemlock; Dust, Wood—Gum; Dust, Wood—Mahogany; Dust, Wood—Maple; Dust, Wood—Oak Mix; Dust, Wood—Pine Mix; Dust, Wood—Redwood; Dust, Wood—Spruce; Dust, Wood—Walnut; Fern Spores; sp.; Flax Fiber; Flaxseed; Hemp; Jute; Kapok; karaya Gum; Lycopodium; Orris Root; Paper Mix; Pyrethrum; Silk; Sisal; Tragacanth Gum; Timothy Hay; Tobacco, Pipe; Tobacco, Cigarette; Tobacco, Cigar; or Tobacco, Leaf.

EXAMPLE 17

Repeating the procedure of Example 11 but replacing the timothy grass pollen extract—BSA conjugate with the BSA conjugate products of Example 7 yields microtiter wells each having adhered thereto a BSA-allergen extract conjugate of Allspice; Almond; Apricot Food; Arrowroot; Artichoke; Asparagus; Avocado; Banana; Bay Leaf; Bean, Kidney; Bean, Lima; Bean, Navy; Bean, Pinto-Frijole; Bean, String/Wax; Beet; Black-Eyed Pea; Blueberry; Brazil Nut; Buckwheat; Cashew Nut; Celery; Cheese, Cheddar (American); Cheese, Parmesan; Cheese, Roquefort; Cheese, Swiss; Cherry Mix; Chewing Gum Base; chicken; Chicory; Chili Pepper; Chocolate/Cocoa; Cinnamon; Clam; Cloves; Cola; Coconut; Codfish Mix; Coffee; Crab; Cucumber; Curry Powder; Date; Dill; Egg White; Egg, Yolk; Eggplant; Endive; Garlic; Gelatine; Ginger; Raisin Mix; Grapefruit; Haddock; Halibut; Hazelnut (Filbert); Herring; Honey; Hops Food; Horseradish; Lamb; Lemon; Lentil; Lime; Liver, Beef (Calves); Lobster; Mackerel; Malt; Mangoes; Maple, Syrup/Sugar; Melon, (see Muskmelon Mix); Milk, Cow's (Albumin); Milk, Cow's (Casein); Milk, Cow's (Whey); Milk, (Evaporated); Milk, Goat's; Mint Mix (Peppermint/Spearmint); Mushroom; Mustard; Nutmeg; Oat, Whole (Grain); Okra; Olive Mix; Onion; Orange, Mandarin/Tangerine; Oregano; Oyster Mix; Papaya; Paprika; Parsley; Parsnip; Pea; Peach Food; Pear Food; Pecan Food; Pepper, Black/White; Pepper, Bell (Green/Red); Perch, Lake; Pineapple; Plum/Prune Mix; Poppy Seed; Pumpkin; Rabbit Meat; Radish; Raspberry; Snapper; Rhubarb; Rice, Wild; Rye, Whole (Grain); Safflower Seed; Sage; Salmon; Scallops; Sesame Seed; Sole; Spinach; Squash, Mix; Strawberry; Sugar (Beet); Sugar (Cane); Sunflower Seeds; Tapioca; Tea; Thyme; Trout; Turkey; Turnip; Vanilla; Walnut Food, Black; Walnut Food, English; Watermelon; Whitefish; Yeast, Brewers; Yeast Mix (Bakers/Brewers, Sacchoromyces cerevisiae).

EXAMPLE 18

Repeating the procedure of Example 11 but replacing the timothy grass pollen extract—BSA conjugate with the BSA conjugate products of Example 8 yields microtiter wells each having adhered thereto a BSA-allergen extract conjugate of *Aspergillus clavatus; Aspergillus glaucus; Aspergillus nidulans; Aspergillus niger; Aspergillus restrictus; Aspergillus sydowi; Aspergillus terreus; Botrytis cinerea; Cephalosporium acremonium; Cephalothecium (Trichothecium) reseum; Chaetomium globosum; Cryptococcus terreus; Cunninghamella elegans; Curvularia spicifera; Dematium nigrum; Epicoccum nigrum; Epidermophyton floccosum; Fomes rimosus; Fusarium vasinfectum; Geotrichum candidum; Helminthosporium maydis; Helminthosporium; Hormodendrum (Cladosporium); Monilia sitophila; Mycogone sp.; Neurospora crassa; Nigrospora sphaerica: Oidiodendrum sp.; Paecilomyces varioti; Pencillium artramentosum; Penicillium biforme; Penicillium carminoviolaceum; Penicillium chrysogenum; Penicillium digitatum; Penicillium expansum; Penicillium glaucum; Penicillium intricatum; Penicillium lutuem; Penicillium roqueforti; Penicillium roseum; Phoma herbarum; Pleospora sp.; Poria sp.; Pullularia pullulans; Rhizopus nigricans; Rhodotorula glutinus; Saccharomyces cerevisiae* (See Yeast Mix); *Scopulariopsis brevicaulis; Spondylocladium* sp.; *Sporobolomyces salmonicolor; Stemphylium botryosum; Streptomyces griseus; Trichoderma viride; Typhula idahoensis: Verticillum alboatrum.*

EXAMPLE 19

Repeating the procedure of Example 11 but replacing the timothy grass pollen extract—BSA conjugate with the BSA conjugate products of Example 9 yields microtiter wells each having adhered thereto a BSA-allergen extract conjugate of Smut, Barley; Smut, Bermuda; Smut Corn; Smut, Johnson; Smut, Oat; Smut, Sorghum; or Smut, Wheat.

EXAMPLE 20

Repeating the procedure of Example 11 but replacing the timothy grass pollen extract—BSA conjugate with the BSA conjugate products of Example 10 yields microtiter wells each having adhered thereto a BSA-allergen extract conjugate of Ants, (Black and Red); Ants, Carpenter; Ants, Fire; Aphid; Bee, Bumble; Bee, Honey; Blackfly; Butterfly; Caddis Fly; Cricket; Cockroach Mix; Deer Fly; Flea antigen; Fruit Flies; Gnat sp.; Horney, Black and Yellow; Horse Fly; House Fly; Mayfly sp.; Mite (D. farinae); Mosquito Mix; Moth, Miller; Wasp; Yellow Jacket; Honey Bee Venom Protein—*Apis mellifera;* Wasp Venom Protein—*Polistes* sp.; White-faced Horner Venom Protein—*Dolichovespula maculata;* Yellow Hornet Venom Protein—*Dolichovespula arenaria;* Yellow Jacket Venom Protein—*Vespula* sp.; or Mixed Vespid Venom Protein.

EXAMPLE 21

In this procedure, timothy grass pollen allergen extract of unknown potency (Unknown) is standardized against timothy grass pollen allergen extract reference standard (Standard) obtained from the United States Bureau of Biologies.

Three-fold serial dilutions of the Unknown and Standard are prepared by standard procedures from extracts which have been reconstituted from the dry (lyophilized) state with 5 ml distilled water per vial. A diluent having the following composition is used for the serial dilution:

| | |
|---|---|
| PO$_4$ buffer solution (PBS), pH 7.5 | 500 ml |
| BSA | 1 g |
| Non-ionic surfactant (Tween 20), 1% v/v | 5 ml |
| Sodium azide, 10 wt. % solution | 0.5 ml |

The serial dilutions were prepared and mixed with serum containing timothy allergen specific IgE (obtained from an atopic patient evidencing timothy pollen allergy) to make dilution sets in microtiter wells for the Standard corresponding to the following TABLE:

| | |
|---|---|
| pH adjusted to | 7.4 |

Serum IgE specific antibody for timothy grass pollen allergen is conjugated to the microtiter plate well surfaces.

To microtiter plate wells 1 to 12 to which a BSA conjugate of timothy grass pollen allergen is adhered is added with mixing 100 microliters of diluted reference Standard extract from a correspondingly numbered serial dilution tube. The procedure is repeated with microtiter plate wells 13 to 24 using serially diluted Unknown extracts from the correspondingly numbered tubes. The mixtures are incubated for 2 hr at room temperature, aspirated and washed three times with buffered rinse solution.

The microtiter plate wells are then contacted with 100 microliters of a solution of alkaline phosphatase conjugated anti-human IgE monoclonal antibody prepared according to a modified procedure of M. O'Sullivan, et al, Analytical Biochem., vol. 100, page 100(1979). The monoclonal antibody is applied in a solution of 0.01M phosphate buffered saline, pH 7.2, containing 4 wt.% polyethylene glycol having a molecular weight of 4000 (PEG 4000), 0.05 wt.% TRITON X-405, 0.1 wt. % BSA, and 0.1 wt.% sodium azide preservative. The alkaline phosphatase conjugated anti-human IgE monoclonal antibody solution is removed from the microtiter plate wells, and they are rinsed

TABLE[a]

| Tube No. | 1 | 2 | 3 | 4 | 5 | 6 | 7 | 8 | 9 | 10 | 11 | 12 |
|---|---|---|---|---|---|---|---|---|---|---|---|---|
| Dilution factor | 0 | 1/3 | 1/9 | 1/27 | 1/81 | 1/243 | 1/729 | 1/2187 | 1/6561 | 1/19683 | 1/59049 | 0 |
| Extract | 0 | 200 | 200 | 200 | 200 | 200 | 200 | 200 | 200 | 200 | 200 | 0 |
| Diluent | 400 | 400 | 400 | 400 | 400 | 400 | 400 | 400 | 400 | 400 | 400 | 400 |
| Total volume | 400 | 600 | 600 | 600 | 600 | 600 | 600 | 600 | 600 | 600 | 600 | 400 |
| Volume added to next tube | 0 | 200 | 200 | 200 | 200 | 200 | 200 | 200 | 200 | 200 | 200[b] | 0 |
| Volume of diluted extract | 400 | 400 | 400 | 400 | 400 | 400 | 400 | 400 | 400 | 400 | 400 | |
| Serum added | 80 | 80 | 80 | 80 | 80 | 80 | 80 | 80 | 80 | 80 | 80 | 80[c] |
| Buffer diluent added | 320 | 320 | 320 | 320 | 320 | 320 | 320 | 320 | 320 | 320 | 320 | 320 |
| Total final volume | 800 | 800 | 800 | 800 | 800 | 800 | 800 | 800 | 800 | 800 | 800 | 800 |

[a] All volumes are in microliters
[b] 200 microliters are discarded
[c] HSA added to provide serum without timothy pollen allergen specific IgE.

The procedure is repeated with tube Nos. 13 to 24 with the Unknown to obtain a corresponding serial dilution act.

A microtiter well product prepared is described in Example 11 having wells to which a BSA conjugate of timothy grass pollen allergen is adhered is soaked for 3–5 minutes with a buffered rinse solution containing 0.85 wt. % sodium chloride, 0.02 wt. % TRITON ×405, 0.01 wt. % BSA, and 0.1 wt. % sodium azide preservative in a 0.0002M aqueous phosphate buffer solution, pH 7.2, and the surplus is removed.

The buffered rinse solution is prepared by diluting the following concentrate with 50 parts by volume distilled or deionized water to one part by volume concentrate:

| | |
|---|---|
| Bovine serum albumin | 0.5 wt. % |
| Non-ionic surfactant (TRITON X-405) | 0.1 wt. % |
| Sodium Chloride | 17 wt. % |
| Sodium azide | 2 wt. % |
| Sodium phosphate | 0.01 M | three times with the buffered rinse solution described above.

To each microtiter plate well is then added 100 microliters of a substrate solution containing $10^{-4}$M 4-methyl umbelliferyl phosphate in 1.25M 2-amino-2-methylpropanol, pH 9.5 in deionized water containing 0.125 mM magnesium chloride and 0.1 wt.% sodium azide. After 60 minutes, the fluorescence level in each well is read with a fluorometer with the excitation at 365 nm and the reading at 450 nm.

The percentage (%) of inhibition of each dilution of Unknown and Standard is determined using the equations $$\% \text{ inhibition} = \frac{(A - a) - (X - a)}{A - a} \times 100\%$$

wherein
  A is the fluorescence signal obtained in carrying out the procedure described above without any allergen extract, X is the fluorescence signal obtained with diluted allergen extract, and a is a blank fluorescence signal obtained in carrying out the procedure described above without any reagent allergen specific IgE.

The (%) inhibitions are as follows:

| | Percentage (%) of Inhibition Timothy Pollen Allergens | |
|---|---|---|
| Dilution | Unknown | Standard |
| 1/3 | 94.8 | |
| 1/9 | 95.4 | 99 |
| 1/27 | 93.5 | 97.4 |
| 1/81 | 88.0 | 93.4 |
| 1/243 | 80.5 | 87.9 |
| 1/729 | 76.0 | 81.3 |
| 1/2187 | 53.4 | 60.5 |
| 1/6561 | 42.6 | 44.5 |
| 1/19683 | 24.0 | 30.8 |
| 1/59049 | 10.0 | 12.5 |

The plot of the (%) inhibitions is shown in the Figure.

By comparing log plots in the Figure of the fluorescence levels measured, as a function of extract concentration (dilution) of the Standard and Unknown extracts, the comparative potency is determined.

EXAMPLE 22

The procedure of Example 21 is repeated with the microtiter plate well products of Examples 12 through 20, inclusive, the respective Standard and Unknown extracts, and with allergen specific reagent IgE specific thereto, the relative potencies of the respective Unknowns are determined.

The invention claimed is:

1. A method for measuring the potency of allergen extracts comprising the sequential steps of
   (a) contacting an insoluble support having reagent allergen adhered thereto with an aqueous solution containing a predetermined amount of allergen extract, and an amount of IgE specific to allergenic components present in the reagent allergen and presumed present in the allergen extract which is insufficient to bind with all of the allergenic components present, for a sufficient time to permit conjugation of IgE with allergenic components, and removing the solution from the support;
   (b) contacting the insoluble support with an aqueous solution of anti-IgE antibody labeled with a fluorogenic enzyme for sufficient time to permit conjugation of anti-IgE antibody with IgE which has conjugated with reagent allergen on the insoluble support, and removing the solution from the support;
   (c) contacting the insoluble support with an aqueous solution of a substrate which undergoes chemical reaction to yield a fluorescent product when in the presence of the fluorogenic enzyme, for sufficient time to yield a fluorescent product; and
   (d) measuring the level of fluorescence in the solution.

2. The method of claim 1 wherein the insoluble support has a plurality of reaction wells separated by opaque material.

3. The method of claim 2 wherein the insoluble support is a microtiter plate made of opaque material.

4. The method of claim 1 wherein the anti-IgE antibody is a monoclonal antibody.

5. The method of claim 1 wherein the anti-IgE antibody is labeled with alkaline phosphatase.

6. The method of claim 5 wherein the substrate is 4-methyl-umbelliferyl phosphate.

7. The method of claim 3 wherein the microtiter plate is polystyrene or a styrene-(vinyl monomer) copolymer.

8. The method of claim 1 wherein the insoluble support is contacted in step (b) with anti-IgE antibody in an aqueous solution containing from 1 to 8 wt.% polyethylene glycol having a molecular weight within the range of from 1000 to 10,000.

9. The method of claim 8 wherein the aqueous solution contains from 0.001 to 0.5 wt. % of a non-ionic surfactant.

10. The method of claim 9 wherein the non-ionic surfactant is octylphenoxypolyethoxyethanol.

11. The method of claim 1 wherein the insoluble support is contacted in step (b) with anti-IgE antibody in an aqueous solution containing from 0.001 to 0.5 wt. % of a non-ionic surfactant.

12. The method of claim 1 wherein the solution is removed from the insoluble support in step (a) by rinsing with a phosphate buffered solution having a pH within the range of from 6 to 8 and containing a non-ionic surfactant.

13. The method of claim 1 wherein the unconjugated anti-IgE antibody is removed from the insoluble support in step (b) with a phosphate buffered solution having a pH within the range of from 6 to 8 and containing a non-ionic surfactant.

14. The method of claim 1 wherein the allergen adhering to the insoluble support is a covalently bonded conjugate of the allergen and a soluble protein or amino acid polymer.

15. The method of claim 14 wherein the allergen adhering to the insoluble support is a covalently bonded conjugate of the allergen and a soluble animal protein.

16. The method of claim 15 wherein the insoluble support is prerinsed with an aqueous buffered solution containing from 0.005 to 2.5 wt. % of the animal protein before being contacted with patient serum.

17. The method of claim 15 wherein the soluble animal protein is bovine serum albumin.

18. The method of claim 17 wherein the insoluble support is prerinsed with an aqueous buffered solution containing from 0.005 to 2.5 wt. % of bovine serum albumin before being contacted with patient serum.

19. The method of claim 15 wherein the allergen is covalently bonded to the bovine serum albumin with a carbodiimide.

20. The method of claim 15 wherein the allergen is covalently bonded to the bovine serum albumin with a bifunctional crosslinking agent.

21. The method of claim 1 wherein the allergen is derived from a pollen, mold, smut, animal dander, animal epidermal, insect, insect venom, dust, or food.

22. The method of claim 1 comprising
   (a) contacting an opaque polystyrene or styrene-(vinyl monomer) copolymer support having a reagent allergen-soluble protein conjugate adhering thereto with an aqueous solution containing a predetermined amount of allergen extract and an amount of IgE specific to allergenic components present in the reagent allergen and presumed present in the allergen extract which is insufficient to bind with all of the allergenic components present, for a sufficient time to permit conjugation of IgE with allergenic components;

(b) removing residual solution from the support;
(c) contacting the support with an anti-IgE antibody labeled with a fluorogenic enzyme in an aqueous solution containing polyethylene glycol and a non-ionic surfactant for a sufficient time to permit conjugation of anti-IgE antibody to any allergen specific IgE conjugated to the support;
(d) removing residual solution from the support;
(e) contacting the support with a solution of a substrate which undergoes reaction in the presence of the fluorogenic enzyme to yield fluorescent product; and
(f) measuring the fluorescence level of the solution.

23. The method of claim 1 wherein steps (a) through (d) are repeated with a corresponding allergen of known potency and the percentage of inhibitions corresponding to the fluorescence levels are compared to determine the relative potency of the allergen extract being measured.

* * * * *

UNITED STATES PATENT AND TRADEMARK OFFICE
CERTIFICATE OF CORRECTION

PATENT NO. : 4,528,267
DATED      : 7/9/85
INVENTOR(S): Emanuel Calenoff, et al

It is certified that error appears in the above-identified patent and that said Letters Patent is hereby corrected as shown below:

On the title page:

In the title, "FLUOROMETIRC", should read --FLUOROMETRIC--

Assignee: "Axionics, Inc., Calif., should read --Axonics, Inc., Calif.--

Column 4, line 23, "Ige" should read -- IgE --.

Signed and Sealed this

Twelfth Day of November 1985

[SEAL]

Attest:

Attesting Officer

DONALD J. QUIGG

Commissioner of Patents and Trademarks